United States Patent [19]
Frantzen et al.

[11] Patent Number: 5,843,164
[45] Date of Patent: *Dec. 1, 1998

[54] INTRALUMINAL STENT FOR ATTACHING A GRAFT

[75] Inventors: John J. Frantzen, Copperpolis; Peter S. Brown, Mountain View; James M. Cannon, Jr., Santa Clara, all of Calif.

[73] Assignee: Advanced Carrdiovascular Systems, Inc., Santa Clara, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 699,172

[22] Filed: Aug. 19, 1996

Related U.S. Application Data

[63] Continuation of Ser. No. 340,112, Nov. 15, 1994, abandoned.

[51] Int. Cl.⁶ ........................................................ A61F 2/06
[52] U.S. Cl. .................................................................. 623/1
[58] Field of Search .......................... 623/1, 12; 606/191, 606/194, 195, 198

[56] References Cited

U.S. PATENT DOCUMENTS

| | | |
|---|---|---|
| 3,657,744 | 4/1972 | Ersek . |
| 3,993,078 | 11/1976 | Bergentz et al. . |
| 4,140,126 | 2/1979 | Choudhury . |
| 4,441,215 | 4/1984 | Kaster . |
| 4,560,374 | 12/1985 | Hammerslag . |
| 4,562,596 | 1/1986 | Kornberg . |
| 4,580,568 | 4/1986 | Gianturco . |
| 4,733,665 | 3/1988 | Palmaz . |
| 4,739,762 | 4/1988 | Palmaz . |
| 4,740,207 | 4/1988 | Kreamer . |
| 4,776,337 | 10/1988 | Palmaz . |
| 4,787,899 | 11/1988 | Lazarus . |
| 4,793,348 | 12/1988 | Palmaz . |
| 4,800,882 | 1/1989 | Gianturco . |
| 4,848,343 | 7/1989 | Wallsten et al. . |
| 4,856,516 | 8/1989 | Hillstead . |
| 4,892,539 | 1/1990 | Koch . |

(List continued on next page.)

FOREIGN PATENT DOCUMENTS

| | | |
|---|---|---|
| 0 177 330 B1 | 6/1991 | European Pat. Off. . |
| 0 461 791 A1 | 12/1991 | European Pat. Off. . |
| 0 479 557 A1 | 4/1992 | European Pat. Off. . |
| 0 480 667 A1 | 4/1992 | European Pat. Off. . |

(List continued on next page.)

OTHER PUBLICATIONS

"Transluminal Expandable Nitinol Coil Stent Grafting: Preliminary Report," by Charles T. Dotter, M.D., et al., in *Technical Developments and Instrumentation*, Apr. 1993.

"Nonsurgical Placement of Arterial Endoprostheses: A New Technique Using Nitinol Wire," by Andrew Cragg, M.D., et al., Apr. 1983.

(List continued on next page.)

*Primary Examiner*—Michael J. Milano
*Attorney, Agent, or Firm*—Fulwider Patton Lee & Utecht, LLP

[57] ABSTRACT

A grant-and-stent combination is disclosed for deploying by an intravascular delivery system at the site of an aneurysm, the combination being expandable from a first diameter to a second, larger diameter to hold open and press the graft against regions of the body lumen just proximal and distal to the aneurysm. The combination is characterized by one or more stents that are flexible due to independently expandable and interconnected cylindrical elements, which provide sufficient radial strength to the combination when the graft-and-stent are being attached to the vessel, but which nonetheless afford sufficient resiliency to allow a great degree of expansion at a rapid rate when the combination is being deployed. Attachment elements in the form of hooks are provided to securely affix the ends of the stent extending distally and proximally of the graft after expansion to the walls of the vessel just distally and proximally of the aneurysm.

10 Claims, 9 Drawing Sheets

U.S. PATENT DOCUMENTS

| | | |
|---|---|---|
| 4,907,336 | 3/1990 | Gianturco . |
| 4,994,071 | 2/1991 | MacGregor . |
| 5,035,706 | 7/1991 | Gianturco et al. . |
| 5,041,126 | 8/1991 | Gianturco . |
| 5,064,435 | 11/1991 | Porter . |
| 5,078,726 | 1/1992 | Kreamer . |
| 5,102,417 | 4/1992 | Palmaz . |
| 5,104,399 | 4/1992 | Lazarus . |
| 5,116,365 | 5/1992 | Hillstead . |
| 5,133,732 | 7/1992 | Wiktor . |
| 5,135,536 | 8/1992 | Hillstead . |
| 5,156,619 | 10/1992 | Ehrenfeld . |
| 5,158,548 | 10/1992 | Lau et al. . |
| 5,161,547 | 11/1992 | Tower . |
| 5,178,618 | 1/1993 | Kandarpa . |
| 5,195,984 | 3/1993 | Schatz ................................. 606/195 |
| 5,207,695 | 5/1993 | Trout, III . |
| 5,211,658 | 5/1993 | Clouse .................................... 623/1 |
| 5,211,683 | 5/1993 | Maginot . |
| 5,219,355 | 6/1993 | Parodi et al. . |
| 5,226,913 | 7/1993 | Pinchuk . |
| 5,242,399 | 9/1993 | Lau et al. . |
| 5,256,150 | 10/1993 | Quiachon et al. . |
| 5,263,963 | 11/1993 | Garrison et al. . |
| 5,275,622 | 1/1994 | Lazarus et al. . |
| 5,282,824 | 2/1994 | Gianturco . |
| 5,304,200 | 4/1994 | Spaulding . |
| 5,304,220 | 4/1994 | Maginot . |
| 5,314,472 | 5/1994 | Fontaine . |
| 5,330,528 | 7/1994 | Lazim . |
| 5,342,387 | 8/1994 | Summers . |
| 5,344,426 | 9/1994 | Lau et al. . |
| 5,354,308 | 10/1994 | Simon et al. . |
| 5,354,309 | 10/1994 | Schnepp-Pesch .................. 606/198 |
| 5,360,401 | 11/1994 | Turnland . |
| 5,387,235 | 2/1995 | Chuter .................................... 623/1 |
| 5,397,355 | 3/1995 | Marin et al. . |
| 5,449,382 | 9/1995 | Dayton .................................... 623/1 |
| 5,527,355 | 6/1996 | Ahn ........................................ 623/1 |
| 5,562,728 | 10/1996 | Lazarus .................................. 623/1 |
| 5,569,295 | 10/1996 | Lam ........................................ 623/1 |
| 5,591,197 | 1/1997 | Orth ........................................ 623/1 |

FOREIGN PATENT DOCUMENTS

| | | |
|---|---|---|
| 0 497 620 A3 | 8/1992 | European Pat. Off. . |
| 0 508 473 A3 | 4/1993 | European Pat. Off. . |
| 0 539 237 A1 | 4/1993 | European Pat. Off. . |
| 540290 | 5/1993 | European Pat. Off. ............ 623/1 |
| 0551 179 A1 | 7/1993 | European Pat. Off. . |
| 0 565 251 A1 | 10/1993 | European Pat. Off. . |
| 0 621 016 | 10/1994 | European Pat. Off. . |
| 0 657 147 A2 | 6/1995 | European Pat. Off. . |
| 0 686 379 A2 | 12/1995 | European Pat. Off. . |
| 43 03 181 | 8/1994 | Germany . |
| 1389778 A2 | 4/1988 | U.S.S.R. . |
| 1457921 A1 | 2/1989 | U.S.S.R. . |
| 1482714 A2 | 5/1989 | U.S.S.R. . |
| WO 90/15582 | 12/1990 | WIPO . |
| WO 92/06734 | 4/1992 | WIPO . |
| 94017754 | 8/1994 | WIPO ........................................ 623/1 |

OTHER PUBLICATIONS

"Radiological Follow–Up of Transluminally Inserted Vascular Endoprostheses: An Experimental Study Using Expanding Spirals," by D. Maass, et al., in *Radiology* 1984.

"Expandable Intraluminal Vascular Graft: A Feasibility Study," by Julio C. Palmaz, M.D., et al., Apr. 5, 1985.

"Percutaneous Endovascular Stents: An Experimental Evaluation," by Kenneth C. Wright, Ph.D., et al., in *Radiology* 1985.

"Atherosclerotic Rabbit Aortas: Expandable Intraluminal Grafting," by Julio C. Palmaz, M.D., et al., in *Radiology* 1986.

"Percutaneous Endovascular Graft: Experimental Evaluation," by David D. Lawrence, Jr., M.D., et al., in *Radiology* 1987.

"Balloon Expandable Intracoronary Stents in the Adult Dog," by Richard A. Schatz, M.D., et al., in *Circulation,* vol. 76, No. 2, 1987.

"Implantation of Balloon–Expandable Intravascular Grafts by Catheterization in Pulmonary Arteries and Systemic Veins," by Charles E. Mullins, M.D., et al., in *Circulation,* vol. 77, No. 1, 1988.

"Elastic Characteristics of the Self–Expanding Metallic Stents," by B.G. Fallone, Ph.D., et al., Dec. 2, 1987.

"Balloon–Expandable Intravascular Stent," by Julio C. Palmaz, M.D., in *Progress in Radiology,* Jan. 22, 1988.

"Self–Expanding Endovascular Graft: An Experimental Study in Dogs," by Tetsuya Yoshioka, et al., in *AJR,* Oct. 1988.

"Transfemoral Intraluminal Graft Implementation for Abdominal Aortic Aneurysms," by J.C. Parodi, M.D., et al., in *Annals of Vascular Surgery,* 1991.

"Intraluminal Bypass of Abdominal Aortic Aneurysm: Feasibility Study," by Jean Claude Laborde, M.D., et al., in *RSNA* 1992.

"Transfemoral Endovascular Aortic Graft Placement," by Timothy A.M., Chuter, BM, BS, et al., in *Journal of Vascular Surgery,* Aug. 1993.

"Endovascular Grafts," by Darwin Eton, M.D., FACS, University of Illinois at Chicago, Mar. 1994.

"Transfemoral Endoluminal Repair of Abdominal Aortic Aneurysm With Bifurcated Graft," by S.W. Yusuf, et al., in *The Lancet,* vol. 344, Sep. 3, 1994.

U.S. Patent Application Serial No. 08/175,214, filed Dec. 28, 1993, entitled Expandable Stents and Method for Making Same (with drawing figures).

U.S. Divisional Application Serial No. 08/214,402, filed Mar. 17, 1994, entitled Expandable Stents and Method for Making Same (with drawing figures).

U.S. Continuation–in–Part Application Serial No. 08/281,790, filed Jul. 28, 1994, entitled Expandable Stents and Method for Making Same (with drawing figures).

FIG. 10
FIG. 11
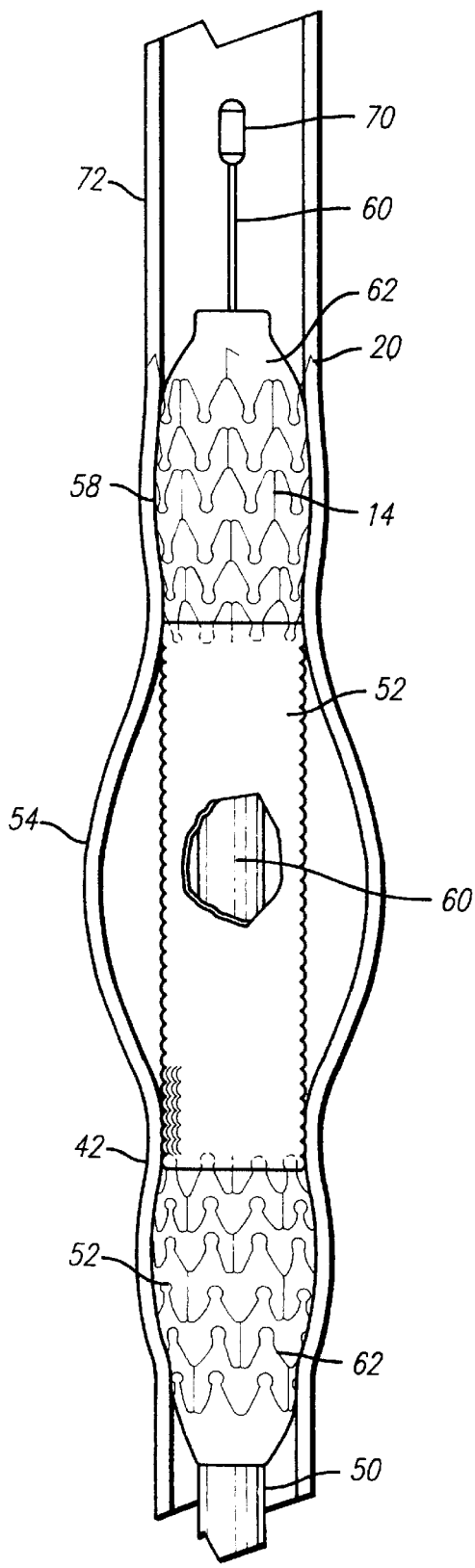
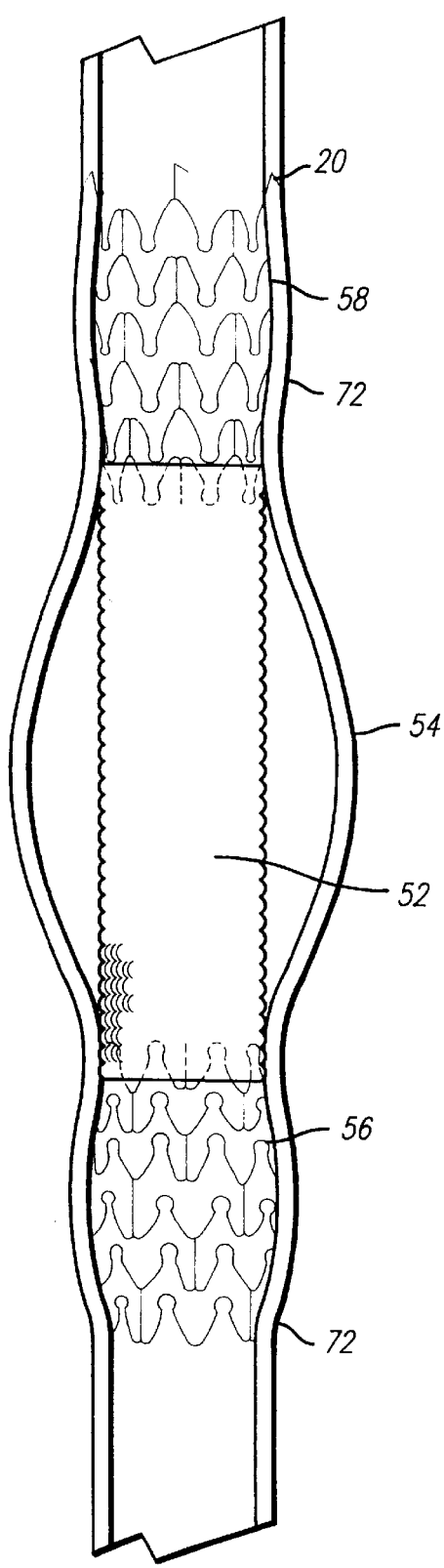

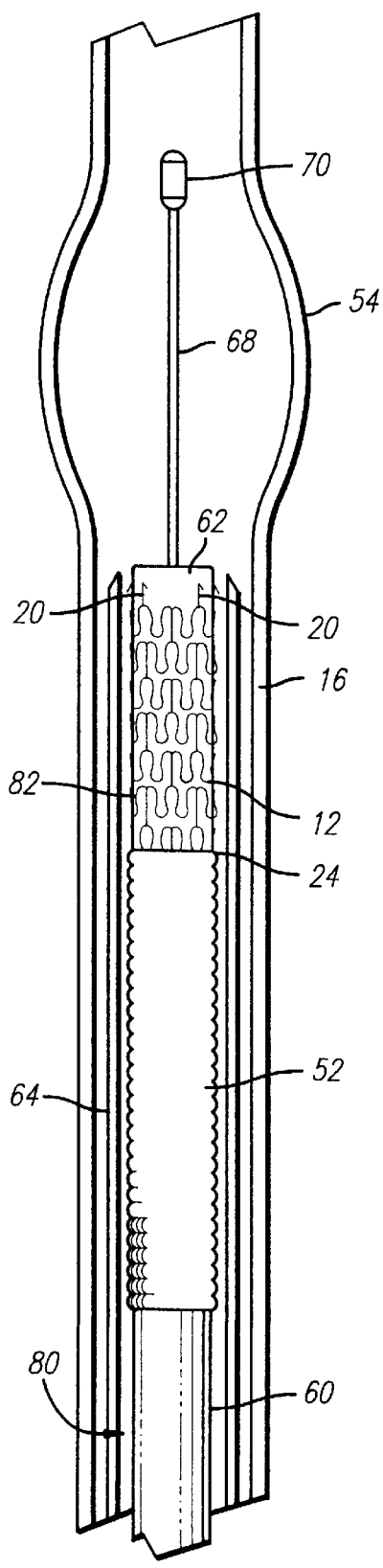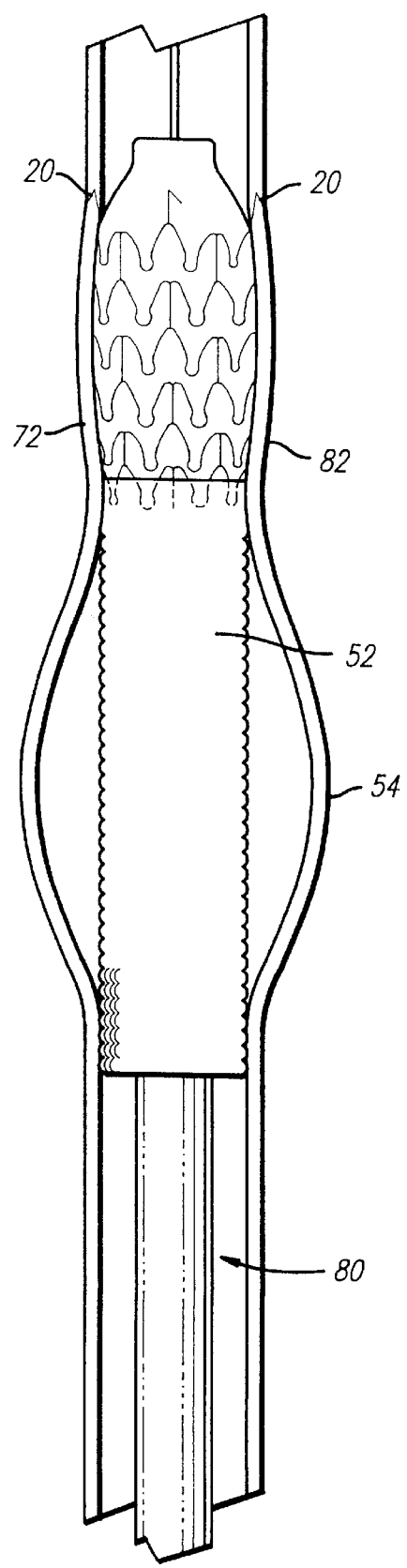

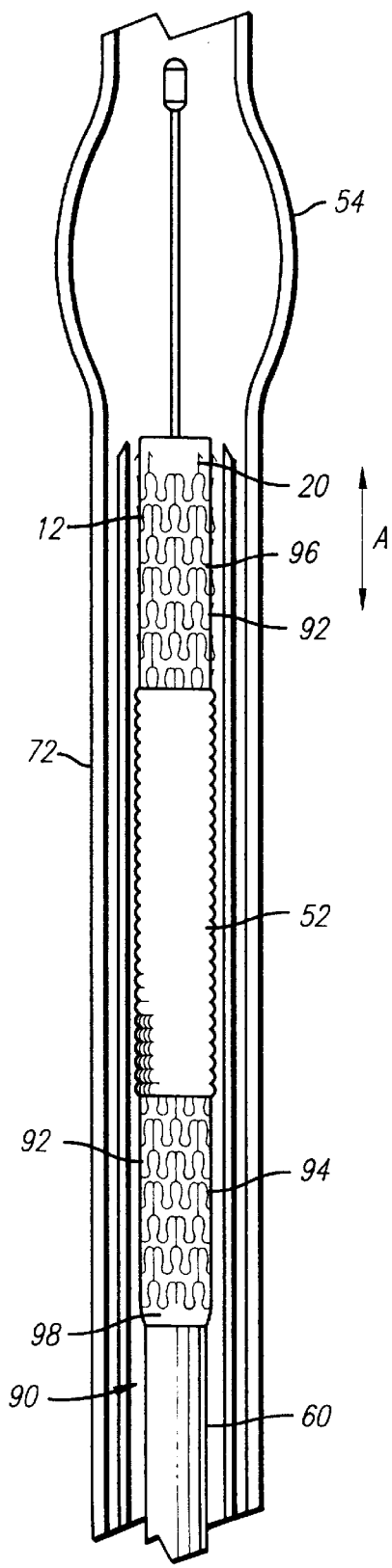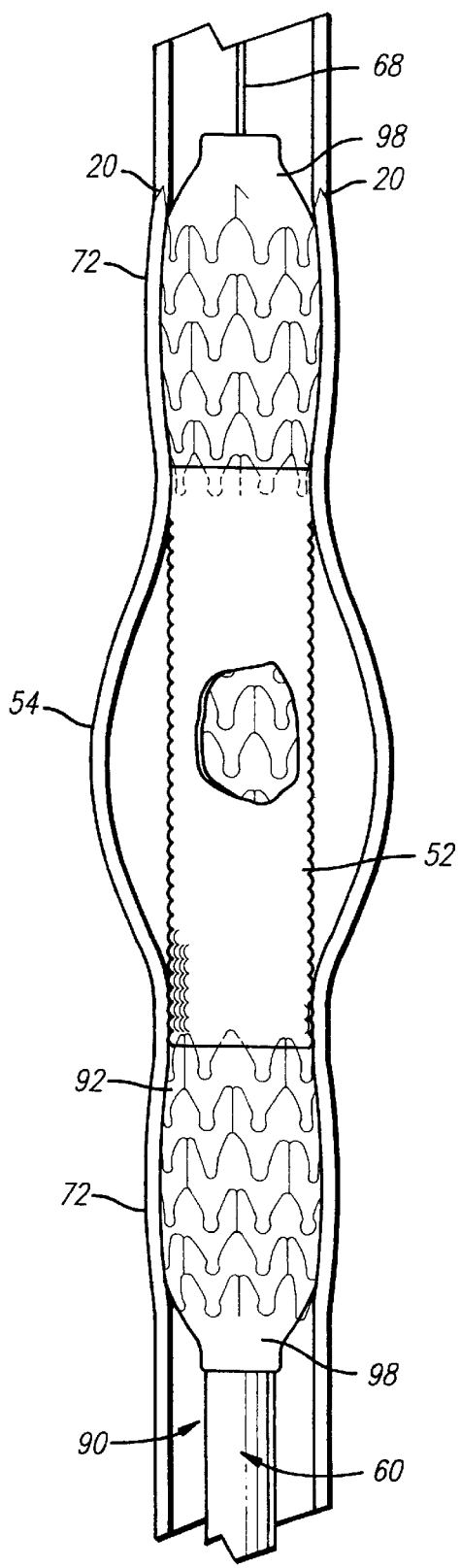

INTRALUMINAL STENT FOR ATTACHING A GRAFT

This application is a continuation of application Ser. No. 08/340,112 filed Nov. 15, 1994 now abandoned.

BACKGROUND OF THE INVENTION

The invention relates generally to endoprostheses and, more specifically, to intraluminal grafts and devices for delivering and deploying the same to an area of a body lumen that has been weakened by damage or disease, such as an aneurysm of the abdominal aorta.

An abdominal aortic aneurysm ("AAA") is an abnormal dilation of the arterial wall of the aorta in the region of the aorta that passes through the abdominal cavity. The condition most commonly results from atherosclerotic disease. Frequently, abdominal aortic aneurysms are dissecting aneurysms, that is aneurysms that are formed when there is a tear or fissure in the arterial lining or wall through which blood is forced and eventually clots, forming a thrombosis which swells and weakens the vessel. Abdominal aortic aneurysms do not cause pain, but are easily detected in a thorough physical examination. If the aneurysm is not detected and treated, it is likely to rupture and cause massive hemorrhaging fatal to the patient.

Treatment of AAAs comprises some form of arterial reconstructive surgery which commonly is referred to as a "triple-A" procedure. One such method is by-pass surgery, in which an incision is made into the abdominal cavity, the aorta is closed off above and below the site of the aneurysm, the aneurysm is resected, and a synthetic graft or tube sized to approximate the diameter of the normal aorta is sutured to the vessel to replace the aneurysm and to allow blood flow through the aorta to be reestablished. The graft commonly is fabricated of a biocompatible material that is compliant and thin-walled. Nylons and synthetic fibers such as those manufactured under the trademarks DACRON or TEFLON have been found to be suitable for the construction of the graft. Studies have shown that the mortality rate associated with this surgical procedure is favorable (less than 5%) when it is performed prior to rupture of an aneurysm. However, patients having an AAA typically are over 65 years of age, and often have other chronic illnesses which increase the risk of perioperative or post-operative complications. Those patients thus are not ideal candidates for this type of major surgery. Further, it has been pointed out that this procedure is not often successfully resorted to after an aneurysm has ruptured (the mortality rate increases to over 65%) because of the extensiveness of the surgery and the time required to prepare a patient for it.

Because of the aforementioned disadvantages to conventional surgical methods, another procedure was developed as an alternative to conventional, major surgery. This method also involves emplacement of a graft at the site of the aneurysm; however, the graft is deployed there by being routed through the vascular system carried by a catheter, wire or other device suitable for negotiating the vasculature. The graft and its deployment system often are introduced into the blood stream percutaneously with a femoral approach and the entire procedure can be performed using local rather than general anesthesia.

Once the graft has been positioned at the aneurysm, it is disengaged from the delivery system and can be affixed to the aortic wall both distally and proximally of the aneurysm. For this purpose, grafting systems usually include fixation means such as staples or hooks which can be manipulated and driven into the intima of the vessel via some mechanical feature of the system, or by some physical process, such as expansion of the graft through application of pressure or temperature change. To avoid premature detachment of the graft and to prevent the attachment elements from damaging the vessels or halting the forward movement of the system while the graft is being routed to the treatment site, the systems often are provided with a feature such as a capsule or a sheath that protects and contains the graft until such time as deployment is desired.

Once the graft is in place, it is positioned in the vessel spanning the site of the aneurysm such that the walls of the graft are generally parallel to the walls of the affected area of the aorta. The aneurysm thus is excluded from the circulatory system by the graft rather than being resected altogether. If the aneurysm is a dissecting type and a thrombosis exists between the walls of the aorta, the now-excluded aneurysm may beneficially provide structural support for the graft.

Grafting systems are known that include what commonly is referred to as an attachment system for deploying the graft. The attachment system is a tubular device which is fitted inside and is generally coaxial with the graft, and which can extend out of the graft at either or both the proximal and distal ends thereof. The attachment system often has a lattice-like or open weave structure, which provides it with flexibility and which promotes rapid endothelial tissue growth through the structure once the graft has been deployed. It may be provided with additional hook-like elements for penetration of the intimal walls for attachment of the graft to the aorta, or those hook-like elements may be provided on the graft itself. Graft systems of type described can be found in U.S. Pat. Nos. 4,787,899 (Lazarus); 5,104,399 (Lazarus); 5,219,355 (Parodi et al.); and 5,275,622 (Lazarus), which are incorporated herein by reference.

The actual function of delivering the graft may be accomplished by inflating a balloon of a catheter by introducing pressurized fluid into a lumen of the catheter from a source external to the patient. Inflation of the balloon applies a force to the graft and any attachment system supplied therein which extends radially and presses the graft and attachment system into the vessel wall just above and just below the aneurysm. When an attachment system is used, disengagement of the catheter from the graft also has been accomplished by taking advantage of the chemical properties of the material from which the attachment system is manufactured. For example, a prior art attachment system may be in the form of a coil of an nickel-titanium alloy, manufactured under the trademark NITINOL™, which will expand radially upon being heated to a higher temperature. The longitudinal dimensions of any attachment system used must account for any reduction in length that might result from radial expansion of the device. Other devices used to attach a graft to the aortic wall for AAA repair include intravascular stents of the type found in U.S. Pat. No. 4,733,665.

In order for a stent to be used most advantageously with a graft deployment system for treatment and repair of aneurysms, the stent must be composed of a biocompatible material and must be simultaneously flexible enough to comply with the catheter or other element used to route the graft through the often tortuous vascular path to the site of the aneurysm and strong enough radially to maintain the opening in the graft once delivered. The stent must be well suited to deployment by a delivery system that is not overly complex, and thus is reliable and easy to operate. Further, it is desirable that the stent be expandable, so that upon application of a force or physical change from within sufficient to cause its radial expansion, it encourages affixation of itself and the graft to the aortic walls. Although various graft delivery systems have been proposed, none adequately provides all of these desirable features.

What has been needed and heretofore unavailable is a stent for use in combination with a graft which has a high degree of flexibility for efficient advancement through tortuous passageways, which can be radially expanded from a relatively small diameter to a relatively large diameter without substantial longitudinal contraction, and which exhibits mechanical strength sufficient to adhere to the vessel walls and to maintain the patency of a synthetic graft implanted at the site of an aneurysm. The present invention satisfies this need.

SUMMARY OF THE INVENTION

The present invention is directed to a stent for use with catheter-graft delivery systems for repairing diseased or injured vessels, and most notably for treating aneurysms, especially aneurysms of the abdominal aorta. The stent of the invention is expandable, so a low profile can be maintained while the graft-and-stent combination is being routed to the aneurysm, and then expanded at the time of deployment to a diameter roughly approximating the diameter of a healthy abdominal aorta and the final diameter of the tubular-shaped graft. Tubular grafts used in the delivery system are conventional and are well known in the art. However, the stent of the present invention that is disposed within the graft is novel and unique. It has a configuration that allows it to expand radially to a much larger diameter than was heretofore possible, and is provided with hooks to penetrate the aortic wall at least above the aneurysm to anchor the graft. The stents are somewhat flexible along their longitudinal axis to facilitate delivery to the treatment site through tortuous blood vessels, but in the expanded condition they are radially stable enough to maintain the patency of the graft and aorta and to attach the combined structure to the aortic walls.

As used herein, reference to the "proximal" is toward the outside of the patient and away from the stent and graft while reference to the "distal" is toward the stent and graft on the balloon portion of the catheter. The proximal and distal references apply to directions in the vascular system and especially the aorta.

In a preferred embodiment, a stent is attached to the distal end of a tubular graft such that at least a portion of the stent is exposed distally beyond the distal end of the graft. The graft-and-stent are deployed intraluminally such that the stent and the distal end of the graft are positioned distally of the aneurysm while the proximal end of the graft extends proximally of the aneurysm. The distal end of the stent is provided with attachment hooks for penetrating healthy tissue in the aortic wall above the aneurysm in order to attach the graft-and-stent combination to the aortic wall. The attachment hooks can have multiple configurations as described herein. Due to the high pressures of blood flow in the aorta, it may be unnecessary to provide attachment hooks in the proximal end of the graft which will be held in place by the pressure of the blood flow. However, under certain conditions attachment hooks in the proximal end of the graft may be warranted.

Thus, in one embodiment, a pair of stents are attached to a tubular graft, one stent at the proximal end and one stent at the distal end of the graft. The stents are oriented so that when both the graft and the stents are expanded to larger diameter states, the stents will be coaxial with the graft. The portions of the stent extending out of the graft are affixed with hooks for penetrating healthy tissue in the walls of the aorta above and below the aneurysm, to aid in attaching the combined structure to the aortic wall. The hooks can have multiple configurations such as one or more barbs, and the barbs can be of various shapes, containing one or more angles, so that the hooks effectively will anchor the graft-and-stent combination to the aortic wall.

Generally, the stent of the present invention includes a plurality of cylindrical elements aligned along a longitudinal axis of the graft. The cylindrical elements are interconnected by at least one interconnecting member, but each cylindrical element is capable of being expanded to a degree in a radial direction independently of other cylindrical elements.

The graft-and-stent combination can be readily delivered to the aneurysm by mounting it on a balloon portion of a delivery catheter, and passing the catheter-graft-stent assembly through the vasculature to the implantation site. A variety of means for securing the graft-and-stent combination to the catheter during delivery is available. Presently, it is preferred to compress the stent onto the balloon and retain the stent and the graft on the balloon using a protective sheath.

Other features and advantages of the present invention will become more apparent from the following detailed description of the invention, when taken in conjunction with the accompanying exemplary drawings.

BRIEF DESCRIPTION OF THE DRAWINGS

FIG. 10 is an elevational view, partially in section, of the stent, graft, and delivery system of FIG. 8, after the graft-and-stent combination has been advanced and deployed in the region of an aneurysm and the stents have been deployed.

FIG. 11 is an elevational view, partially in section, of the graft-and-stent combination of FIGS. 9 and 10, after the combination has been deployed and the catheter withdrawn.

FIG. 12 is an elevational view, partially in section, of another means by which a stent according to the invention can be incorporated into a graft delivery system, depicting the system prior to advancement of the graft-and-stent combination into the region of an aneurysm.

FIG. 13 is an elevational view, partially in section, of the delivery system of FIG. 12 after the graft-and-stent combination has been advanced and partially deployed in the region of an aneurysm.

FIG. 14 is an elevational view, partially in section, of an alternate means by which a stent according to the invention can be incorporated into a graft delivery system, depicting the system prior to deployment of the graft-and-stent combination.

FIG. 15 is an elevational view, partially in section, of the delivery system of FIG. 14, depicting the system during deployment of the graft-and-stent combination.

DETAILED DESCRIPTION OF THE PREFERRED EMBODIMENTS

The invention relates to an intravascular stent, one or more of which is used in conjunction with a known tubular graft for repairing body lumens of all types. As described herein, reference is made to repairing an aortic aneurysm, however, other body lumens are equally suited to receive the graft-and-stent combination of the present invention.

Figure 1:
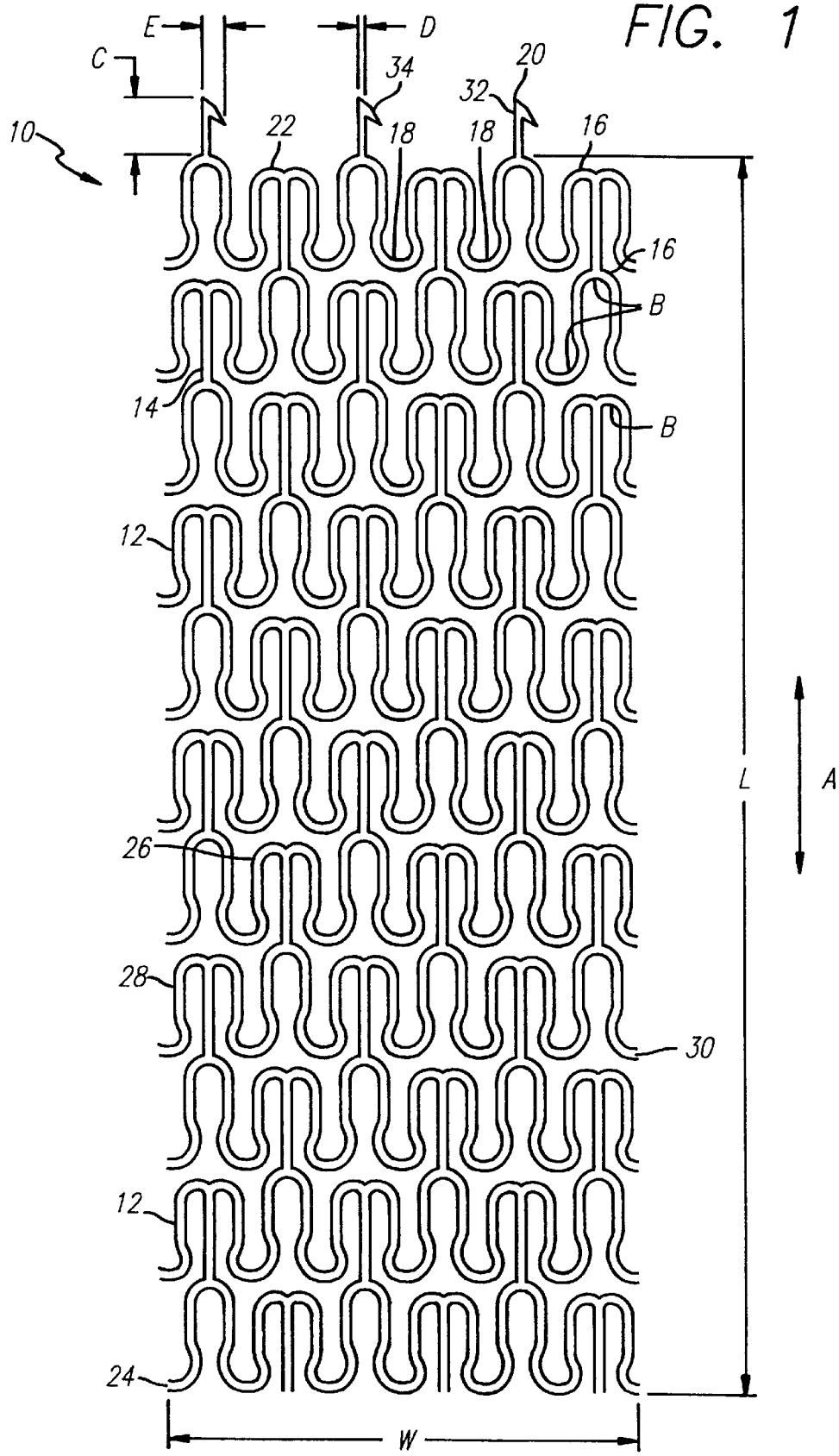
FIG. 1 is a plan view depicting the stent having hooks at one end and prior to rolling into a cylindrical configuration.

FIG. 1 depicts stent 10 incorporating features of the invention, in the state the stent would appear if flattened prior to rolling into a cylindrical configuration. The stent generally is comprised of a plurality of cylindrical rings 12 which are spaced close enough together to allow the stent to provide a reliable means of attaching the graft at the treatment site, but are not so tightly spaced as to inhibit the flexibility of the combination. The cylindrical rings are connected to each other by connecting members 14. Each cylindrical ring is characterized by serpentine or wave pattern, having a series of alternating peaks 16 and valleys 18. The degrees of curvature indicated by arrows B along adjacent peaks and valleys are different and, preferably, the pattern of each cylindrical ring is in phase with the pattern of every other cylindrical ring. Attachment elements 20, shown in FIG. 1 in the form of hooks, can be provided on first end 22 of the stent, to engage with the aortic wall when the stent is deployed. Second end 24 of the stent will be attached to the graft when the graft-and-stent combination is assembled. As is described more fully below in relation to FIGS. 8–11, when two stents 10 are used in combination with a single graft, only the stent situated at the most distal end of the graft need be provided with attachment elements in order to adequately anchor the combination to the vessel. In FIG. 1, the configuration of the hooks is such that each is positioned at every other peak 18 that is at first end 22 of the stent, which will comprise the most distal end of the stent when it is fully formed and oriented for deployment. Each hook has shaft portion 32 extending outwardly from the distal most cylindrical ring, and barb portion 34 extending from the shaft.

The expansion properties of stainless steel make it a preferred material for stent 10. As is set forth more fully below, the stent, including the hooks, can be formed from a flat sheet of material by chemically etching, laser cutting, or electronic discharge machining (EDM) and the like. It also is contemplated that the hooks may be formed independently of the stent and subsequently attached to it by welding, brazing or another process with the equivalent effect. The body has width W and length L, which length will be parallel with longitudinal axis A of the stent when the body is rolled into a cylinder. To secure the cylinder, lengthwise edges 28 and 30 of the body can be connected with a suitable means such as by welding, brazing, soldering or with adhesives. A YAG laser is particularly suitable for welding lengthwise edges 28,30 together (See FIG. 2).

In a presently preferred embodiment, as shown in FIG. 1, it is contemplated that a stent with the dimensional characteristics disclosed below would be suited for use with a graft in triple-A procedures with a variety of vascular anatomies. It is clear, however, that a stent with other dimensions might be equally useful in a graft delivery procedure. Preferably, stent 10 is formed from a flat sheet of stainless steel. For a flat sheet, prior to being rolled into a cylindrical shape, width W of the stent is approximately 0.63 inches (16 mm), while length L of the stent, exclusive of hooks 20, is in the range of about 0.2 to 2.0 inches (5.1 to 50.8 mm) It is desirable for connecting members 14 to have a transverse cross-section similar to the transverse dimensions of the undulating components of the expandable bands. The shaft of each hook has length C of approximately 0.05 inch (1.3 mm) and diameter (or width) D of approximately 0.008 inch (0.2 mm). The barbs of the hooks have width E of approximately 0.03 inch (0.8 mm). As stated, these dimensions are preferred, but the selection of the most appropriate dimensions in a particular clinical situation may vary considerably from patient to patient.

Figure 2:
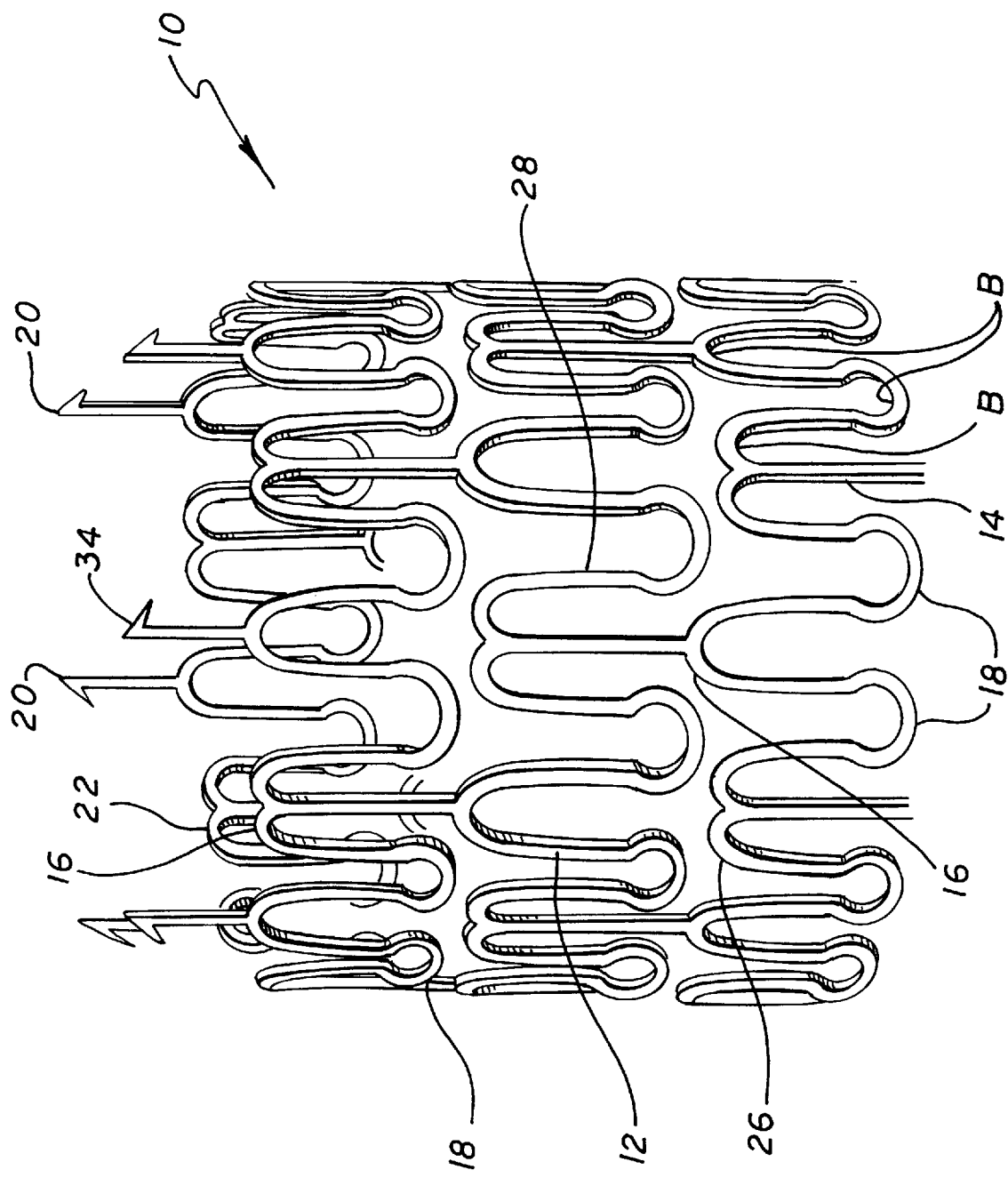
FIG. 2 is a perspective view of a portion of the stent of FIG. 1 rolled into a cylindrical configuration with only the top ring fully depicted for clarity.
Figure 3:
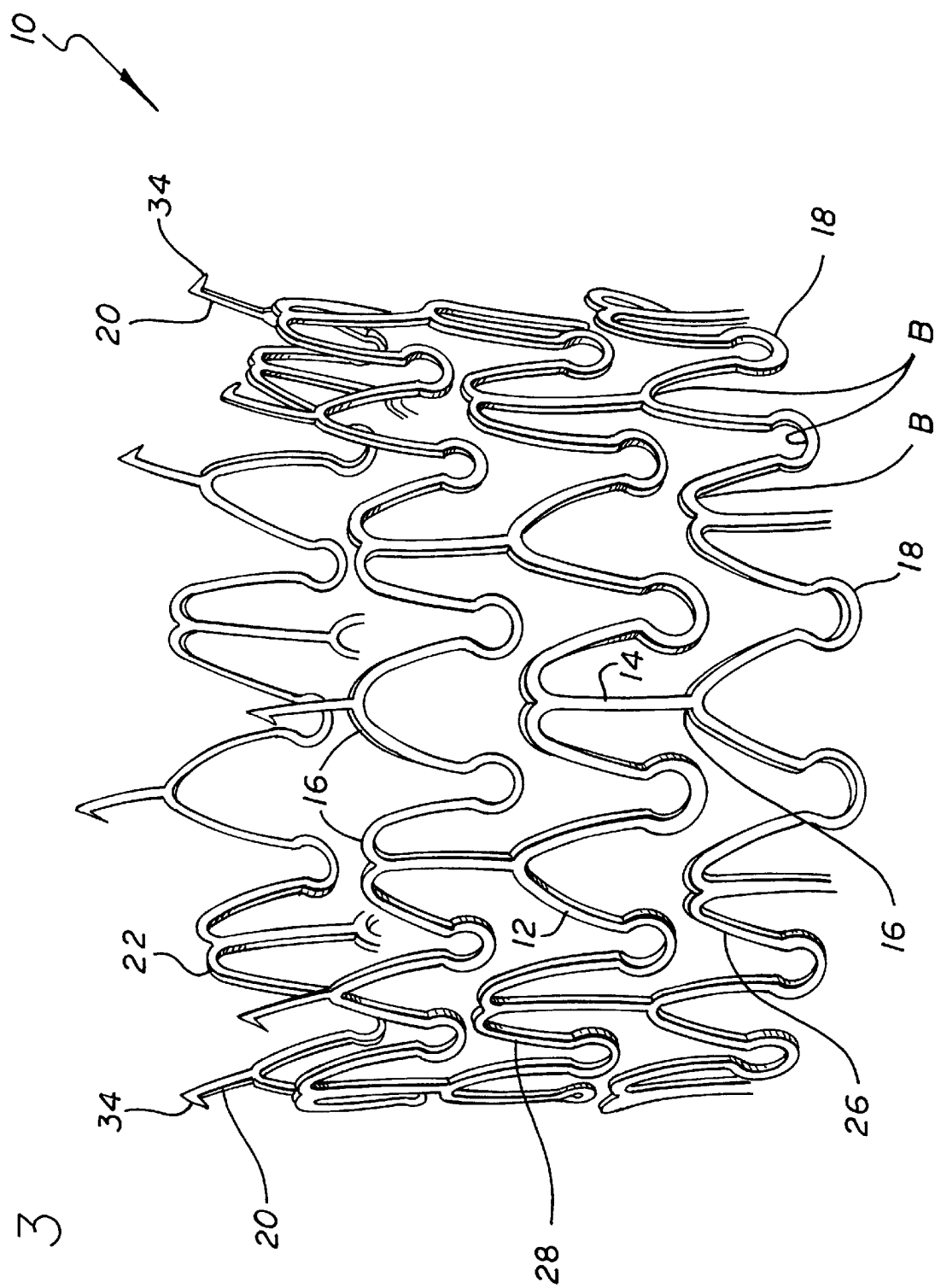
FIG. 3 is a perspective view of a portion of the stent of FIG. 1 rolled into a cylindrical configuration and expanded, again with only the top ring fully depicted for clarity.

After stent 10 has been rolled into its cylindrical shape from a flat sheet, as seen in FIG. 2, the unique features of the device are such as to allow the stent to be uniformly expanded in a radial direction, FIG. 3, both to a significant degree and without large variation in the level of diametric expansion of each cylindrical ring. The cylindrical rings 12 are transverse to the longitudinal axis A of the finished stent, and the varying degrees of curvature B between peaks 16 and valleys 18 tend to equalize the stresses experienced by the stent during expansion, so that the peaks and valleys of each band deform radially with substantial uniformity upon application of an expansion force. The novel structure permits the stent to increase from an initial, small diameter to any number of larger diameters (See FIG. 3). When the interconnections 14 between two cylindrical rings are aligned with the interconnections between all other cylindrical rings, such that the attachment is accomplished by traversing the distance between the peaks 16 of consecutive cylindrical rings, the serpentine pattern of each cylindrical ring is in phase with the pattern of every other ring. This manner of connection of the cylindrical rings thus minimizes the degree to which the stent will be shortened or will contract along its longitudinal axis when it is expanded radially about longitudinal axis A. This configuration also limits twisting of the stent upon expansion and it enhances more uniform expansion. The in-phase cylindrical ring patterns further are thought to reduce the likelihood that the stent or any portion of it will recoil, or collapse back to its starting diameter after deployment.

The number and orientation of connecting members of stent 10 can be varied in order to maximize the desired longitudinal flexibility of the stent structure both in the unexpanded and in the expanded condition. Flexibility is advantageous during deployment of the graft and stent because it improves the ease and safety with which the combination can be delivered through the vascular system to the aneurysm. Following affixation of the stent to the aortic wall, longitudinal flexibility minimizes alteration of the natural physiology of the aorta due to the implant and helps to maintain compliance of the portions of the vessel supporting the graft. The discrete bands also have the capacity to rotate slightly with respect to each other without causing any significant alteration of the basic cylindrical structure of the stent. Accordingly, the cylindrical rings and connections cumulatively result in a stent that is very flexible along its length or longitudinal axis, but which provides uniform expansion and is very stable and resistant of collapse. The reticulated structure supplied by the patterning allows for the perfusion of arterial blood into the region of the aortic wall to which elements 18 are attached to anchor the graft and stents or graft and stent in place. Such perfusion promotes assimilation of the synthetic prostheses by the aorta and, more generally, healing of the treated site.

The more uniform radial expansion of this design results in a stent 10 that can be expanded to a large diameter without substantial out-of-plane twisting, because no high stresses are concentrated in any one particular region of pattern 24. Rather, the forces are evenly distributed among the peaks 16 and valleys 18, allowing the cylindrical rings 12 to expand uniformly. Minimizing the out-of-plane twisting experienced by the stent during delivery and deployment of the graft-and-stent combination also carries with it the benefit of minimizing the risk of thrombus formation. The special expansion characteristics of the stent of the invention also allow any portion of the stent that extends distally or proximally of the graft to continue to expand even when the graft has achieved its maximum cross-sectional dimension, so as to more securely affix the graft-and-stent combination to the vessel above and below the aneurysm.

The uniformity in stress distribution further reduces the likelihood that fractures in stent 10 will occur due to stresses applied to any particular region or cylindrical ring 12 of the stent. This feature also contributes to the ability of the stent to be expanded to a greater degree and at a faster rate than was feasible previously with other designs. Radial strength is not sacrificed upon expansion and the degree to which expansion causes longitudinal contraction, and thus a shortening of the stent, is minimal.

Figure 4:
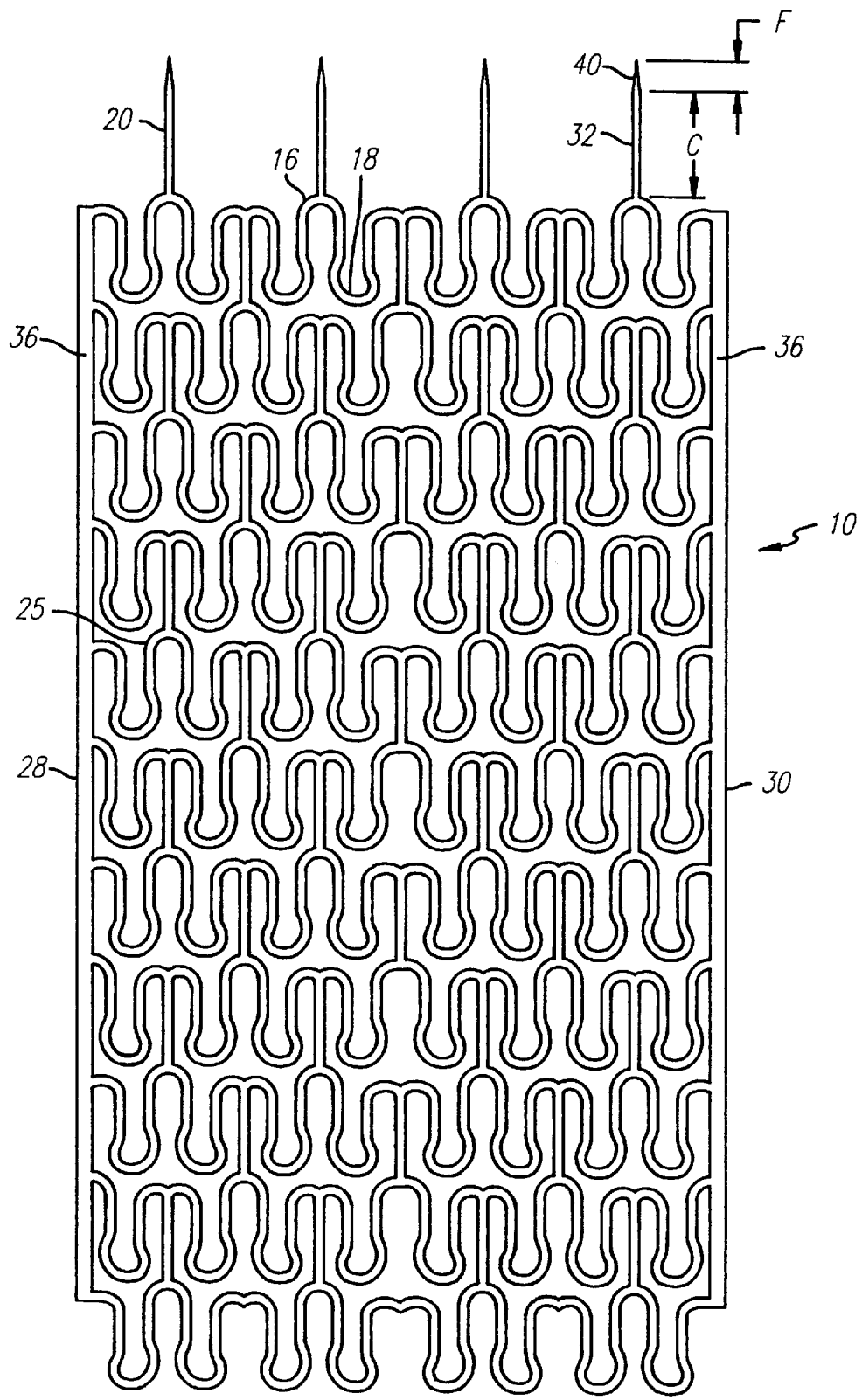
FIG. 4 is a plan view depicting the stent in a flattened form and having support bars on the edges for welding when the stent is rolled into a cylindrical form and it includes spikes for attachment means.

In keeping with the invention, attachment elements 20 can be provided in a variety of shapes and configurations to insure adequate attachment of one or more stents 10 while the healing process to assimilate the stent into the aortic wall of the aorta through endothelial tissue growth is taking place. In FIG. 4, attachment elements 20 are in the form of spikes rather than hooks, being straight and having sharply pointed tips at the end of the shafts. Length C and length F of shafts 32 and tips 40 respectively, is approximately 0.05 (1.3 mm). When stent 10 is expanded, some of peaks 16 or valleys 18 of cylindrical ring 12, or portions thereof, which extend distally or proximally of the graft, may tip outwardly, becoming embedded in the aortic wall and forcing the spikes also to become lodged in the vessel, thus aiding in retaining the stent in place as the stent becomes permanently implanted. Support bars 36 are provided at lengthwise edges 28 and 30 of stent body 26, to provide support material for a joint. As stent 10 is rolled into a cylindrical form, edges 28,30 can abut or overlap and are then permanently affixed to each other by known means such as laser welding, brazing, soldering, epoxy, and the like.

Figure 5:
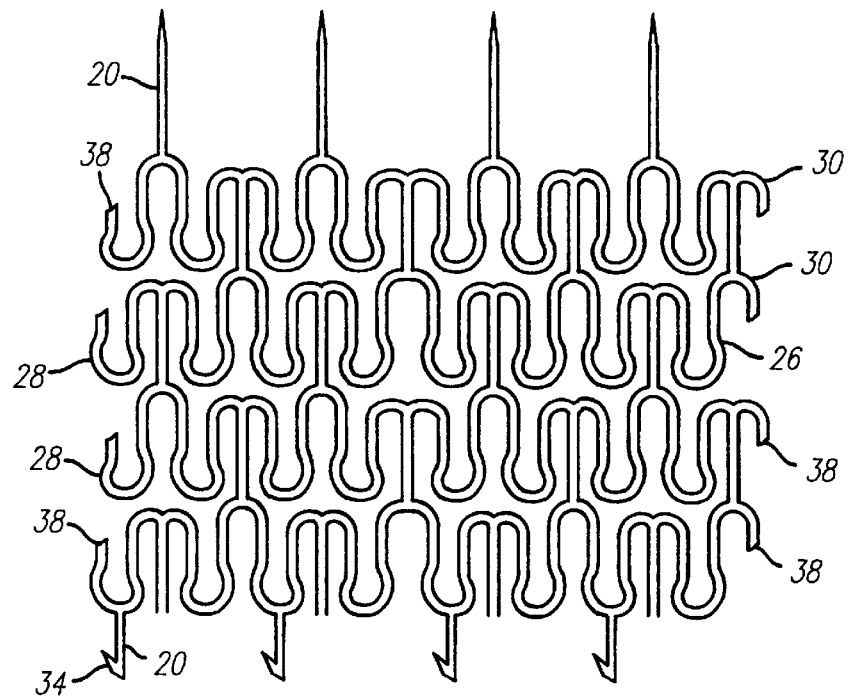
FIG. 5 is a plan view of the stent depicting alternative attachment means and lap joints which mate when the stent is rolled into a cylindrical configuration.

Still another embodiment of the stent of the stent of the invention is shown in FIG. 5. As in FIG. 4, attachment elements 20 are configured as spikes instead of barbed hooks. In lieu of support bars 36, lengthwise edges 28 and 30 of stent body 26 are provided with lap joints 38, which allow the stent to be mechanically secured as a cylinder. The lap joints 38 are configured to mate when stent 10 is rolled into its cylindrical configuration. The lap joints 38 are attached to each other by welding, brazing, soldering, or the application of an epoxy or an adhesive. Attachment hooks 20 having a barb portion 34 may also be formed on the stent end opposite attachment spikes.

Figure 6:
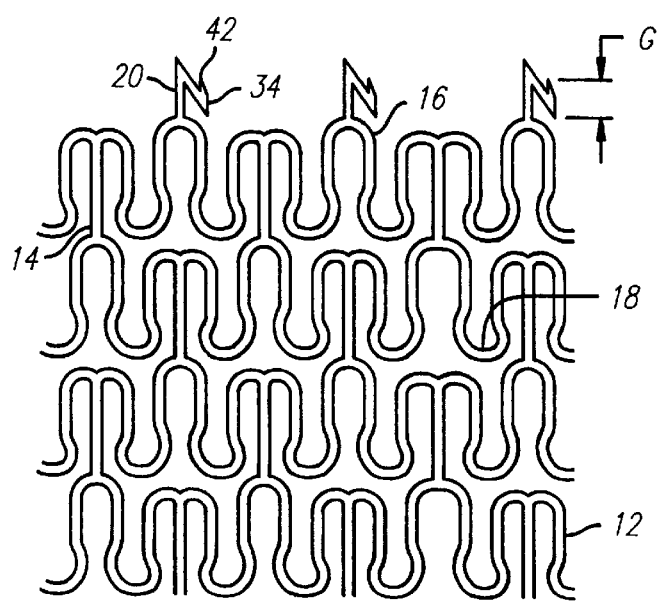
FIG. 6 is a plan view of the stent depicting an alternate embodiment of the invention having attachment hooks with barbs.
Figure 7:
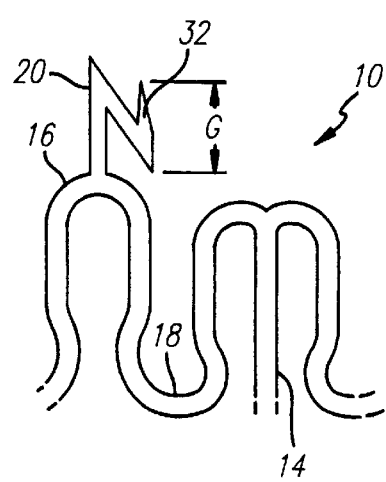
FIG. 7 is an enlarged partial plan view of the stent of FIG. 6 depicting the attachment hooks having barbs.

Another embodiment of attachment elements 20 is illustrated in FIGS. 6 and 7. Barbs 34 with dimensions similar to those of the barbs of FIG. 1 are provided, however, the barbs further are equipped with tail portions 42, which have length G of approximately 0.05 inch (1.3 mm). Again, the dimensions set forth herein only are for illustration purposes and will vary widely depending upon the application and the patient. It can be readily appreciated that many other types of attachment elements 20 may be affixed to or formed unilaterally with the stent body without departing from the scope of the invention. For example, multiple barbs can be provided spaced apart from each other on the shaft of a single attachment element for more than one anchor site per element. The angles formed between the shafts and barbs can vary and can be selected so as to best accomplish the anchoring function in a given application. Many other shapes and configurations are contemplated that are designed to optimize the attachment of the end of the stent to the aortic wall while the healing process is taking place to assimilate the stent and graft into the vessel by endothelial tissue growth.

Details of the various processes by which the stainless steel stent can be manufactured can be found in commonly owned and assigned U.S. Pat. Nos. 5,569,295 to Lam and 5,514,154 to Lau et al., which hereby are incorporated herein in their entirety by reference. Briefly, the stainless steel stent can be formed by a chemical etch process out of a flat sheet or a piece of tubing. The areas of stainless steel to remain are identified by covering the regions with a material resistant to the chemicals used in the etching process, such that when the metal is exposed to the chemicals, the openings or reticles in the patterned structure are created by reaction of the chemicals with the unprotected areas of the steel. The etching process develops smooth openings in the sheeting or tubing devoid of burrs or other artifacts that can be characteristic of other processes when products of the small sizes contemplated here are manufactured. An electropolishing process may be used after the chemical etching is complete in order to polish the stent surface. The stent surface can be polished to an approximately 5 to 10 micro inch finish.

There are numerous advantages in chemically etching a flat sheet of material, such a stainless steel, into the stent of the present invention. For example, chemical etching is economical since a large number of stents can be chemically etched on the same flat sheet at the same time. The chemical etching process creates no burrs and the surface finish of the eventual inside diameter of the stent can be improved by electro-polishing on one side only. Further, chemical etching creates no extra heat treating to the parts that are being processed. The raw material wall thickness and grain structure is more uniform in a flat sheet as opposed to chemical etching a stainless steel tube. Further, in a flat sheet, the bevel of the etching can be controlled, whereas when tubing is etched, the bevel creates a thicker part on the inside diameter and a thinner part on the outside diameter.

An important advantage of chemical etching the stent of the present invention from a flat sheet of stainless steel material is that a process known as "step etching" can be used. For example, by using step etching in the areas of the spikes 20 in FIG. 3, it is possible to remove portions of material so that the spikes will bend outwardly when the stent is expands. In other words, step etching allows for the removal of material in highly selective areas so that upon radial expansion of the stent, areas having less material will have a tendency to bend or distort, such as with the spikes bending outwardly to engage the aortic wall.

Photo-lithographic techniques also can be employed for the manufacture of the stents, using a computer-controlled laser patterning process to remove the chemically resistive coating applied to the metal sheet or tube. A plurality of stents can be formed from one length of sheeting or tubing, by repeating the stent pattern and providing small webs or tabs to interconnect the stents. After the etching process, the stents can be separated by severing the small webs or tabs. Subsequently, if the stents were formed on a sheet, the individual stents are rolled and the edges welded together to provide a cylindrical configuration.

Yet another method of making the stent of the present invention is by the commonly known process of electronic discharge machining (EDM). Using EDM, the stainless steel stent can be formed from a flat sheet or from a section of tubing.

When stent 10 of the present invention is made from a material that is difficult or impossible to detect under fluoroscopy, such as stainless steel, it is desirable to incorporate radiopaque markers to identify the position of the graft-and-stent assembly during deployment. The stent 10 of the present invention can be coated with a metal film that is radiopaque, such as gold, silver, platinum, tantalum and the like. One method of coating the stent of the present invention with a radiopaque marker is disclosed in copending U.S. Ser. No. 08/233,046 which is incorporated herein by reference.

One preferred method of incorporating the stent of the present invention into a graft delivery system is illustrated in FIGS. 8–11. Delivery system 50 is used to deploy tubular graft 52 at the site of abdominal aortic aneurysm 54 via stents 56 and 58. The structure of stents 56 and 58, the materials from which the stents are made, and the processes that might be used to form the stents are set forth in detail in connection with the discussion of FIGS. 1–7. It is contemplated that this use of the stent could be accomplished with a wide variety of graft types. Due principally to the ability of the stent of the invention to expand rapidly from a very small diameter to a much larger diameter without substantial shortening, a stent with a relatively short length can be used. The graft used in this delivery system is sized so that its cross-section substantially matches that of the healthy portion of the aorta.

Delivery system 50 includes multilumen catheter 60 of the type used in other percutaneous procedures for deploying stents and other prostheses to repair portions of blood vessels. The catheter has a first lumen extending along its length which is in communication with two expandable members or balloons disposed at the distal end of the catheter. The balloons are spaced apart for a distance that is slightly less than the length of the shortest graft intended to be deployed using the system. Pressurized fluid or gas can be introduced into the balloon lumen to inflate the balloons, to exert an outward radial force on anything disposed about the balloon.

After stents 56 and 58 have been attached to graft 52, the graft-and-stent combination is loaded onto the distal end of catheter 60. The combination is positioned so that each stent overlies a balloon 62 and the graft rests over and is substantially coaxial with the portion of the catheter that is between the two balloons. In order to insure that the graft and stents remain in this position until the deployment function is accomplished, the two stents are compressed or "crimped" onto the balloons prior to insertion of delivery system 50 into the patient. The graft and stents also can be secured by positioning the stents between ridges or collars provided on the expandable members, which will restrain lateral movement of the combination. Alternatively, biodegradable adhesives might be used to temporarily affix the stents to the balloons, the adhesives being subject to degradation and absorption by the body when it is desired to deploy the graft.

Catheter 60 further is provided with sheath 64 that helps to hold the graft and stents onto the catheter and which prevents direct contact of the elements of the combination with the walls of the vessels while the system is being advanced to the treatment site, thus protecting the vascular system of the patient from any sharp edges on the stents. Rod or wire 66 or other suitable mechanical element is connected to the sheath and extends proximally along the length of the catheter so that it can be manipulated by the physician exterior to the patient and retracted (proximally) at the time of deployment. Alternatively, a sheath can be provided that traverses the entire length of the catheter, and can be retracted (proximally) from outside the patient to expose the graft-and-stent combination.

The catheter has a second lumen through which guidewire 68 passes. The guidewire advantageously is advanced through the vasculature of a patient beyond the site of aneurysm 54 as a preliminary step in the graft delivery procedure. After the guidewire has been positioned, the catheter carrying the graft and stents is advanced over the guidewire. Although a particular form of catheter has been described to route the graft-and-stent combination to the aneurysm, it will be apparent to those skilled in the art of treating aneurysms and similar conditions and of percutaneous catheter design that catheters of various configurations or wires and rods or the like could be used successfully to perform the same function. For example, well known fixed wire and rapid exchange wire systems also can be used in the delivery system described herein.

Attachment elements or hooks 20 are provided on the most distal end 22 of stent 58, which hooks ultimately will attach the graft-and-stent combination to regions in the intima aortic wall. If desired or necessary to achieve a more secure attachment, hooks also can be provided on the proximal end of stent 56 for attaching to the aortic wall 72 at a point proximal to the aneurysm. The hooks anchor the stents and the graft while the implantation process is on going, and before the body has naturally assimilated the combination through intergrowth of endothelial cells.

Figure 8:
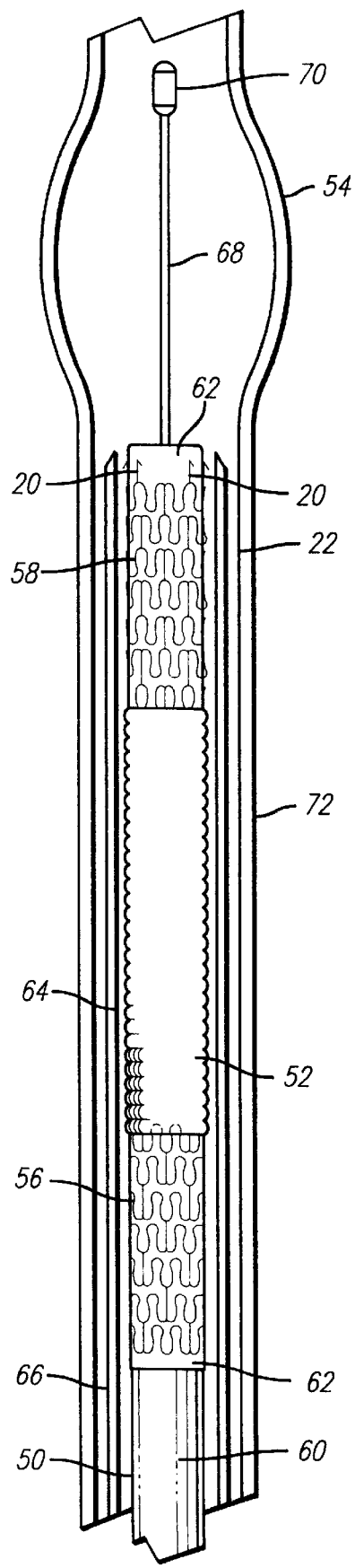
FIG. 8 is an elevational view, partially in section, of the stents of the invention incorporated into a graft and a delivery system, which can deliver and deploy the stents and graft.
Figure 9:
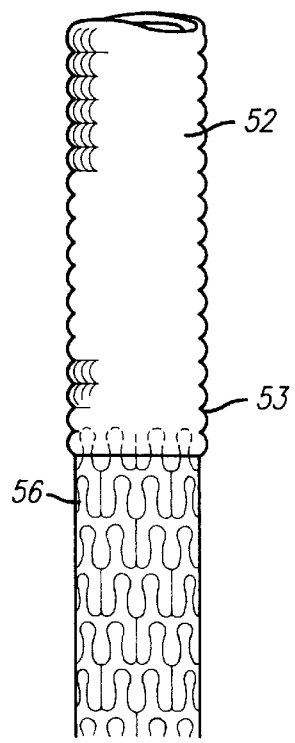
FIG. 9 is an enlarged partial view of one of the stents shown in FIG. 8 attached to the graft.

As is shown in FIG. 8, stent 56 and stent 58 each are affixed to an end of graft 52 by staples 53. Other appropriate means might be used, such as a biocompatible adhesive, for example an epoxy resin, to attach stents 56,58 to graft 52. Alternatively, the stent might be sewn onto the graft at selected points. At least a portion of stents 56,58 extend out of graft 52, and if the stents and graft are joined by a butt joint, then substantially all of the stent will extend out of the graft.

In FIG. 8, all of the elements of graft delivery system 50 except the distal end of guidewire 68 are shown positioned proximally of aneurysm 54, before graft 52 and stents 56 and 58 have been deployed. Sheath 64 of catheter 60 covers the graft and stents disposed about balloons 62, and the distal end of the guidewire has entered the region of the aorta that is affected by the aneurysm. In FIG. 10, the sheath is withdrawn (proximally) exposing the graft-and-stent combination and the catheter is advanced so that the graft-and-stent combination span the aneurysm. The balloons 62 are inflated by the pressurized fluid or gas source external to the patient, and the radial forces accompanying expansion of the balloons are applied to expand both the graft and the stents radially outward, pressing both elements against aortic wall 72 proximal to and distal to the aneurysm. Hooks 20 provided on the stent 58 become embedded in the aortic wall 72, to anchor the graft-and-stent combination against downstream arterial pressure while the healing process takes place. In FIG. 11, the delivery apparatus has been withdrawn and the graft-and-stent combination is in final position across the aneurysm and attached to healthy tissue in aortic wall 72. It should be understood that when tubular graft 52 is expanded it is not stretching or deforming but is simply opening from a closed diameter to an open and expanded diameter. The graft material is generally inelastic and can be made from any number of materials compatible with the body such as DACRON®, TEFLON®, and polymeric materials.

Another preferred method of incorporating a stent according to the present invention into a graft delivery system is illustrated in FIGS. 12 and 13. This embodiment differs from that shown in FIGS. 8–11 in that a single stent is used to anchor the graft in FIGS. 12–13 while two stents were used in FIGS. 8–11. A single stent is appropriate in the aorta where blood pressures can exceed 100 mm/Hg, which is enough force to hold the proximal end of the graft in place without the need for an anchoring stent on the proximal end of the graft.

Delivery system 80 (FIGS. 12–13) is shown in the abdominal aorta, just proximal to aneurysm 54. A single stent 82 is attached by its proximal end 24 to the distal end of graft 52 by staples, adhesive, or by sewing or other appropriate means as previously described. The graft-and-stent combination is mounted on catheter 60 and the stent is crimped or compressed onto balloon 62. Retractable sheath 64 covers and protects both the graft-and-stent combination during delivery through the vascular system until sheath 64 is withdrawn proximally to allow deployment of the combination. Hooks 20 extend from the most distal cylindrical element 12 to attach the graft and stent to aortic wall 72. As can be understood with reference to FIGS. 12 and 13, the stent is affixed to the distal end of the graft so that it substantially extends out of the graft, with the result being that radial expansion forces can be applied to the stent by inflating balloon 62 of catheter 60 and simultaneously applying expansion force to graft 52. The stent is expanded simultaneously with the graft to drive hooks 20 into aortic wall 72 in healthy tissue distal to aneurysm 54, to anchor the combination to the vessel.

Another embodiment using the stent of the present invention in a graft delivery system is illustrated in FIGS. 14 and 15. Delivery system 90 includes stent 92 which is coaxial with and which extends the length of and beyond graft 52, such that first portion 94 of stent 92 extends proximally of graft 52 and second portion 96 extends distally of the graft. The most distal cylindrical element 12 of stent 92 is equipped with hooks 20, which will be relied upon at the time of deployment to anchor the graft-and-stent combination to healthy aortic tissue while the prosthesis is accepted by the body of the patient.

Balloon 98 necessarily must have a much greater length when measured along a longitudinal axis A of stent 92 than the balloons of previously described embodiments, because the stent of this embodiment is at least double the length of either of the two stents used in the preferred method of delivering the graft and of the stent used in the embodiments of FIGS. 8–13.

As can be seen with reference to FIG. 15, stent 92 and graft 52 which overlies it are positioned so that the graft spans the length of aneurysm 54. Balloon 98 then is inflated with pressurized fluid or gas to expand both the graft and the stent simultaneously and to force hooks 20 into engagement with aortic wall 72 distally of the aneurysm. The expandable member then is deflated and the delivery system withdrawn leaving the graft-and-stent combination in place in the blood vessel.

While the invention has been illustrated and described herein in terms of its use as an endoprosthesis for implanting a graft to treat an aneurysm, it will be apparent to those skilled in the art that the stent can be used in other instances in other vessels of the body. Because the stent of the present invention has the novel features of attachment elements and the capacity to expand quickly from relatively small diameters to relatively large diameters, the stent is particularly well suited for implantation in almost any vessel where such devices can be used. This feature, coupled with the fact that the stent does not contract or recoil to any great degree after it is radially expanded, provides a highly desirable support member for other types of endoprosthesis. Other modifications and improvements may be made without departing from the scope of the invention.

What is claimed is:

1. A longitudinally flexible stent for implanting in a body lumen and expandable from a contracted condition to an expanded condition, comprising:

a plurality of adjacent cylindrical elements each having a circumference extending around a longitudinal stent axis and each element being substantially independently expandable in the radial direction, said elements being arranged in alignment along the longitudinal stent axis;

said cylindrical elements formed in a generally serpentine wave pattern transverse to the longitudinal axis and containing a plurality of alternating peaks and valleys;

at least one interconnecting member extending between adjacent cylindrical elements and connecting them to one another;

said serpentine pattern having varying radii of curvature at least in regions of said peaks, the varying radii of curvature being selected to provide a generally uniform radial expansion of said cylindrical elements and a generally uniform expansion of said serpentine pattern around the circumference of each cylindrical element during expansion of the stent from the contracted condition to the expanded condition;

a plurality of hooks and spikes on the stent for attaching the stent to the body lumen; and the stent, hooks, and spikes formed of a unitary structure such that upon radial expansion of the stent the spikes bend outwardly and engage the body lumen wall.

2. The stent of claim 1, wherein said varying radii of curvature are dimensioned so that the bending stress developed at said peaks and valleys during radial expansion of said cylindrical elements is uniform around the circumference of said cylindrical elements.

3. The stent of claim 1, wherein the varying radii of curvature of said peaks are dimensioned relative to the stress created during expansion of the stent from the contracted condition to the expanded condition.

4. The stent of claim 1, wherein said valleys have varying radii of curvature that is different than said radii of curvature of said peaks.

5. The stent of claim 1, wherein said adjacent cylindrical elements are connected to each other by a plurality of said interconnecting members whereby said stent expands from a first smaller diameter to a second enlarged diameter without appreciable change in overall length.

6. The stent of claim 1, wherein said cylindrical elements cooperate to define a generally cylindrical surface and wherein said peaks form projecting tips which project outwardly from said cylindrical surface upon expansion.

7. The stent of claim 1, wherein said plurality of hooks are configured to penetrate the body lumen to more securely attach the stent to the body lumen.

8. The stent of claim 1, wherein said plurality of hooks are configured to penetrate all the way through the body lumen.

9. The balloon expandable stent of claim 1, wherein said unitary structure is formed by chemically etching a flat sheet.

10. The balloon expandable stent of claim 1, wherein said unitary structure is formed by chemically etching a tubular member.

* * * * *